US00PP19050P3

(12) United States Plant Patent
Kaagman

(10) Patent No.: US PP19,050 P3
(45) Date of Patent: Jul. 29, 2008

(54) ***OSTEOSPERMUM* PLANT NAMED 'OSTE YEL'**

(50) Latin Name: *Osteospermum ecklonis*
Varietal Denomination: Oste Yel

(75) Inventor: Pim Kaagman, Andijk (NL)

(73) Assignee: Goldsmith Seeds Europe B.V., Andijik (NL)

( * ) Notice: Subject to any disclaimer, the term of this patent is extended or adjusted under 35 U.S.C. 154(b) by 134 days.

(21) Appl. No.: 11/393,158

(22) Filed: Mar. 29, 2006

(65) Prior Publication Data

US 2007/0240246 P1 Oct. 11, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

PUBLICATIONS

UPOVROM PBR 20042598 Plant Variety database for plant OSTE YEL 1 page.*

* cited by examiner

*Primary Examiner*—Annnette H Para
(74) *Attorney, Agent, or Firm*—Jondle & Associates, P.C.

(57) ABSTRACT

An *Osteospermum* cultivar particularly distinguished by large, deep-yellow inflorescences with brown eyes, green foliage with incised leaves, an upright and medium-sized plant habit, inflorescences that are induced at higher temperatures, continuous flowering throughout the Summer, good heat tolerance, vigorous growth, excellent rooting characteristics and a good shipping ability, is disclosed.

2 Drawing Sheets

Genus and species: *Osteospermum ecklonis* Norl.
Variety denomination: 'Oste Yel'.

BACKGROUND OF THE NEW PLANT

The present invention comprises a new and distinct cultivar of *Osteospermum,* botanically known as *Osteospermum ecklonis* Norl., and hereinafter referred to by the cultivar name 'Oste Yel'. The new cultivar originated from a hybridization made in the Summer of 2002 in Andijk, The Netherlands. The female parent was the proprietary 'OX-7-1' (unpatented) *Osteospermum* plant, having yellow inflorescences, while the male parent was the proprietary 'OZ-185-1' (unpatented) *Osteospermum* plant, having lemon-colored inflorescences.

The new cultivar was created in 2002 in Andijk, The Netherlands, and has been asexually reproduced repeatedly by vegetative cuttings and tissue culture in Andijk, The Netherlands, Gilroy, Calif. and Hillscheid, Germany over a three-year period. The present invention has been found to retain its distinctive characteristics through successive asexual propagations.

Plant Breeder's Rights for this cultivar have been applied for in Canada on Mar. 31, 2005 and with the European Union on Dec. 20, 2004.

SUMMARY OF THE INVENTION

The following are the most outstanding and distinguishing characteristics of the new cultivar when grown under normal horticultural practices in Andijk, The Netherlands and Hillscheid, Germany.

1. Large, deep yellow inflorescences with brown eyes;
2. Green foliage with incised leaves;
3. Vigorous growth 4. An upright plant and medium-sided plant habit;
5. Inflorescences that are induced at higher temperatures (so that a cool cultivation period is not necessary);
6. Continuous flowering throughout the Summer (in contrast to older varieties that do not develop inflorescences in the mid-Summer);
7. Good heat tolerance;
8. Excellent rooting characteristics; and
9. Good shipping ability.

DESCRIPTION OF THE PHOTOGRAPHS

This new *Osteospermum* plant is illustrated by the accompanying photographs which show overall plant habit including inflorescences, buds, and foliage of the plant; the colors shown are as true as can be reasonably obtained by conventional photographic procedures. The photos are of a 12-14-week-old plant grown in a 12-cm pot in a greenhouse in Spring 2005.

DESCRIPTION OF THE NEW CULTIVAR

Figure 1:
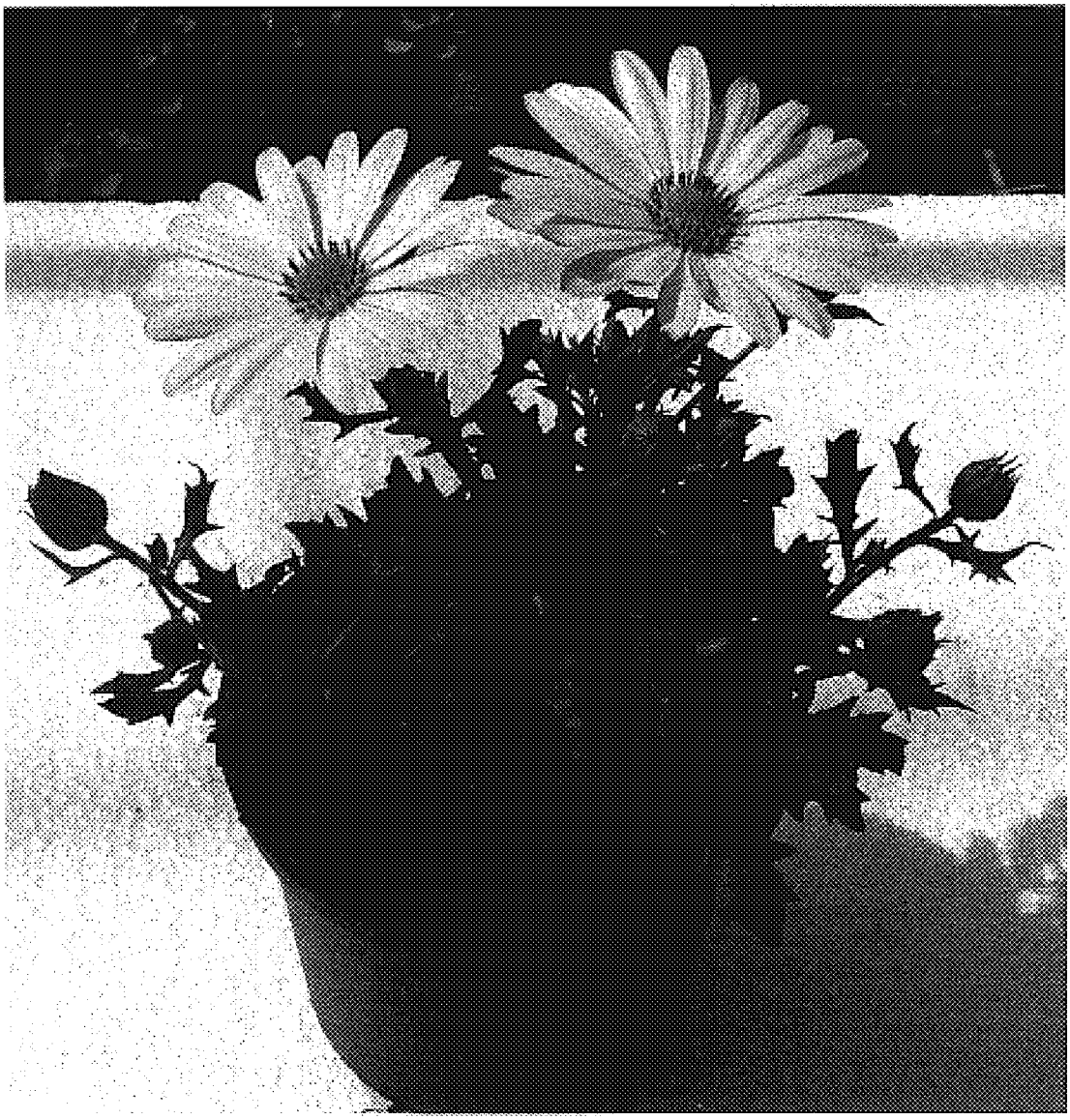
FIG. 1 shows the overall plant habit, including blooms, buds, mature foliage, and plant habit.
Figure 2:
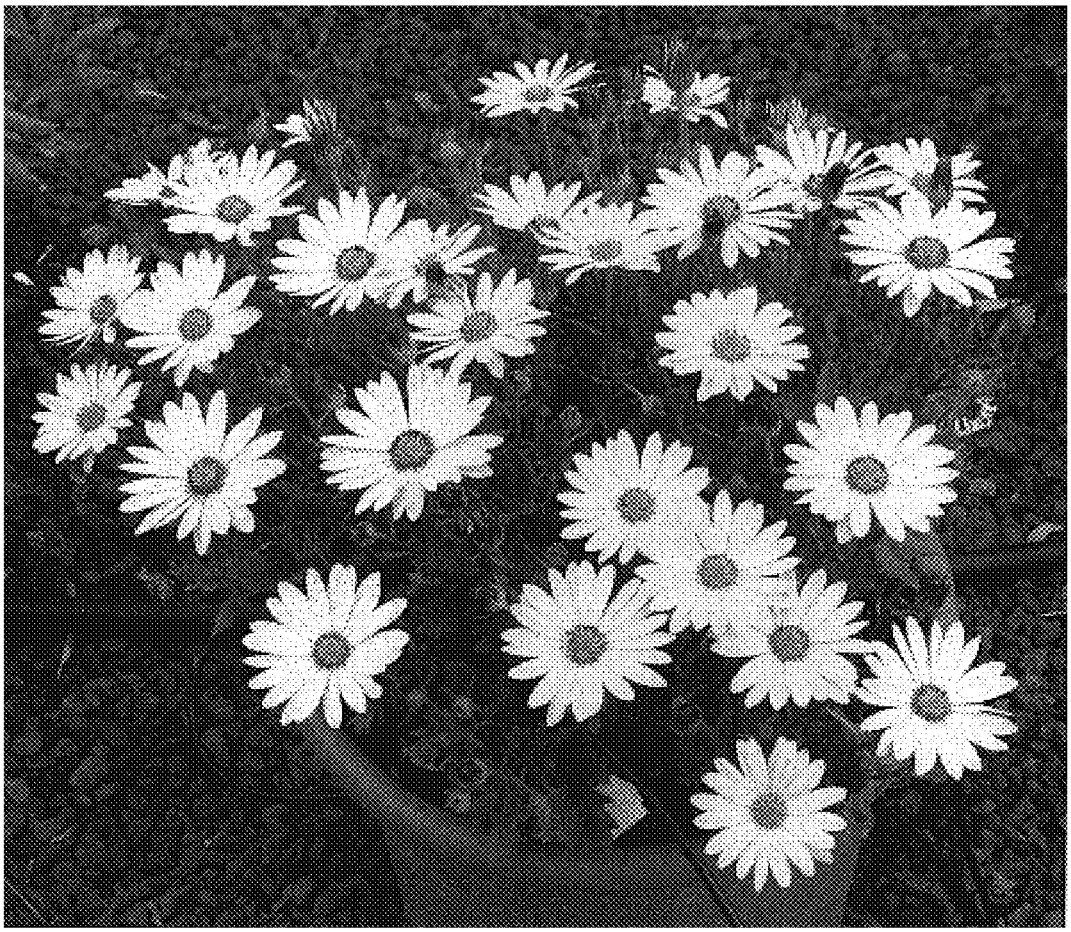
FIG. 2 shows the mature inflorescences.

The following detailed descriptions set forth the distinctive characteristics of 'Oste Yel'. The data which define these characteristics were collected from asexual reproductions carried out in Hillscheid, Germany. The plant history was taken on 10-week-old, un-pinched plants grown in 12-cm pots in a greenhouse during late Summer. The color readings were determined under natural light in mid-May from flowers grown in a greenhouse. Color references are to the RHS Colour Chart of The Royal Horticultural Society of London (R.H.S.) (2001).

DESCRIPTION OF THE NEW PLANT

Classification:
*Family.*—Asteraceae.
*Botanical name.*—*Osteospermum ecklonis* Norl.
*Common name.*—African daisy.

Parentage:
*Female parent.*—The proprietary 'OX-7-1' (unpatented) *Osteospermum* plant having yellow inflorescences.
*Male parent.*—The proprietary 'OZ-185-1' (unpatented) *Osteospermum* plant having lemon-colored inflorescences.

Plant:
*Form and habit.*—Herbaceous perennial but usually cultivated as an annual.
*Growth and branching habit.*—Fairly vigorous, upright, un-pinched plants develop none to few basal branches; pinching plants once or twice enhances flowering.
*Height* (*from top of soil, including inflorescence*).—36 cm.
*Width* (*including inflorescences*).—22 cm.
*Time to produce a finished flowering plant.*—13 to 15 weeks for a 12-cm pot in the Spring.
*Outdoor plant performance.*—Use as bedding plants or in mixed-container plantings.
*Time to initiate and develop roots.*—About 24 days.
*Root description.*—Fibrous, freely branching.

Leaves:
*Arrangement.*—Simple and alternate.
*Shape.*—Relatively small, oak-leaf-shaped but with more pointed lobes.
*Apex.*—Acute.
*Base.*—Acute or attenuate.
*Margin.*—Incised with strong lobes.
*Texture.*—Leathery.
*Immature leaf.*—Color: Upper surface: RHS 137D. Lower surface: RHS 143A.
*Mature leaf.*—Color: Upper surface: RHS 137B (deep-green). Lower surface: Between RHS 137D and RHS 143A. Length: Up to 5.0 cm. Width: 2.6 cm.
*Petioles.*—Length: 1.5 cm to 2.0 cm. Diameter: 0.3 cm to 0.4 cm. Color (both sides): RHS 145B. Texture: Short, weak pubescence.

Stems:
*Total number of branches.*—5 to 8.
*Length.*—28 cm to 32 cm.
*Diameter.*—0.4 cm.
*Internode length.*—1.5 cm.
*Color.*—RHS 146D (green), partly RHS 178A (reddish-brown) with anthocyanin when outdoors.
*Texture.*—Sparse hair.

Inflorescence buds:
*Shape.*—Initially round; elongate with the development of the ray florets.
*Diameter* (*horizontal*).—1.2 cm.
*Height.*—1.8 cm.
*Color* (*at tight bud just before the ray florets unfold*).—RHS 166D (brown) and RHS 12B (yellow).

Inflorescence:
*Type.*—A capitulum or composite-type; solitary inflorescences are borne terminally above the foliage.
*Blooming habit.*—Continuously flowers from Spring through Fall.
*Quantity of inflorescences per plant.*—5.
*Lastingness of the inflorescences on the plant.*—About 14 days.
*Fragrance.*—None.
*Inflorescence diameter.*—9.0 cm to 9.5 cm.
*Inflorescence depth.*—About 2.0 cm.
*Disc diameter.*—1.8 cm.

Disc floret:
*Quantity per inflorescence.*—50.
*Shape.*—Tube-shaped, while the upper end is 5-lobed.
*Tube color* (*closed*).—RHS 143C (greenish).
*Tube color* (*mature*).—RHS N155B (whitish).
*Length.*—0.4 cm.
*Diameter* (*at apex*).—0.2 cm to 0.3 cm.
*Apex.*—Acute.
*Apex color.*—RHS 11B (pale-yellow).
*Base.*—Tube-shaped, narrow.
*Margin.*—Entire.

Ray floret:
*Quantity per inflorescence.*—18 to 22.
*Shape.*—Oblanceolate.
*Color.*—Upper surface: From RHS 12A (golden-yellow) near the base, to RHS 13A for the main part. Lower surface: RHS 13B (yellow), with a central stripe of RHS 166B (brown-orange).
*Length.*—4.3 cm.
*Width.*—1.1 cm.
*Apex.*—Rounded to obtuse.
*Base.*—Acute.
*Margin.*—Entire.
*Texture.*—With parallel veins, appears somewhat rippled lengthwise; white hair (pappus) at the base.
*Peduncle.*—Length: About 5.0 cm. Diameter: 0.3 cm, furrowed or grooved near the inflorescence base. Texture: Short, coarse pubescence. Color: RHS 143B.

Phyllaries:
Arrangement. —In a whorl, partly adhere to the bases of the ray florets.
*Observed, quantity per plant.*—15 to 18, with an average number of 15.
*Shape.*—Lanceolate.
*Color.*—Upper surface: RHS 137D (green). Lower surface: RHS 137D (green).
*Length.*—0.6 cm to 1.2 cm.
*Width.*—0.1 cm to 0.3 cm.
*Apex.*—Acute.
*Base.*—Fused.
*Margin.*—Entire.
*Texture.*—Densely pubescent.

Reproductive organs:
*Androecium.*—Location. Present on disc florets only (stick out from the relatively indistinct disc florets and let the mature disc appear mainly brown). Stamen quantity: One per floret. Stamen shape: Tube-shaped, cylindrical. Filament color: RHS 155A (whitish), upper part RHS N186C. Anther color: RHS N188C (deep purple-brown). Stamen length: 0.4 cm to 0.5 cm. Pollen color: RHS 17A (orange). Pollen amount: Abundant.
*Gynoecium.*—Location: Present on ray florets only. Number: One per floret. Pistil length: 0.6 cm. Stigma color: RHS 178B (reddish-brown). Stigma shape: 2-lobed. Style color: RHS 8A (yellow). Style length: 0.2 cm to 0.3 cm. Style shape: Fliform (filament-like) with the lobes of the stigma slanting upright (bifurcate).

Fruit and seed set: Seed set has not been observed.
Disease and insect resistance: Average/typical of the species; not special observations made.

COMPARISON WITH PARENTAL AND COMMERCIAL CULTIVARS

'Oste Yel' differs from the female parent 'OX-7-1' (unpatented) in that 'Oste Yel' has inflorescences on shorter peduncles so that 'Oste Yel' has a more compact plant habit than 'OX-7-1'. In addition, 'Oste Yel' has an earlier flowering response than 'OX-7-1'.

'Oste Yel' differs from the male parent 'OZ-185-1' (unpatented) in that 'Oste Yel' has larger, deeper-yellow inflorescences and thinner leaves than 'OZ-185-1'.

'Oste Yel' differs from commercial cultivar 'Kakegawa AU6' (U.S. Plant Pat. No. 12,781) in that 'Oste Yel' has larger, deeper-yellow inflorescences than 'Kakegawa AU6'. 'Oste Yel' has deep-green leaves with strong lobes, while 'Kakegawa AU6' has longer and narrower leaves that are greyish-green with shallow lobes. In addition, 'Oste Yel' has a narrower plant habit with shorter stems than 'Kakegawa AU6'.

'Oste Yel' differs from the commercial cultivar 'Sunny Alex' (unpatented) in that 'Oste Yel' has darker green foliage, an earlier flowering response and a more compact plant habit than 'Sunny Alex'.

I claim:

1. A new and distinct cultivar of *Osteospermum* plant as shown and described herein.

* * * * *